United States Patent [19]

Suyama et al.

[11] Patent Number: 4,587,978
[45] Date of Patent: May 13, 1986

[54] APPARATUS FOR HIGH-FREQUENCY HYPERTHERMIA

[76] Inventors: Sumio Suyama, Kojohga-oka 15-25, Ohtsu-shi, Shiga-ken; Itsuo Yamamoto, Tsutsumi-cho 3-chome 17-10, Yao-shi, Osaka, both of Japan

[21] Appl. No.: 660,351

[22] Filed: Oct. 12, 1984

[30] Foreign Application Priority Data

Oct. 31, 1983 [JP] Japan .................. 58-205424

[51] Int. Cl.$^4$ ................................ A61N 1/06
[52] U.S. Cl. .................... 128/804; 128/798
[58] Field of Search ............ 128/804, 420, 420 A, 128/421, 422, 423, 783, 798; 250/515.1, 516.1

[56] References Cited

U.S. PATENT DOCUMENTS

| | | | |
|---|---|---|---|
| 2,623,549 | 12/1952 | Archer | 250/516.1 |
| 3,045,121 | 7/1962 | Leguillon | 250/516.1 |
| 4,140,130 | 2/1979 | Storm, III | 128/798 |
| 4,196,355 | 4/1980 | Maine | 250/516.1 |
| 4,269,189 | 5/1981 | Abraham | 128/798 |

Primary Examiner—Kyle L. Howell
Assistant Examiner—Randy Citrin
Attorney, Agent, or Firm—Griffin, Branigan & Butler

[57] ABSTRACT

An apparatus for high-frequency hyperthermia wherein a pair of electrodes having round holes and thereby annularly shaped are attached to the surface of the body of a patient so as to interpose therebetween an affected part located in the depth of the body. The electrodes are disposed in such a manner that the affected part is allowed to be collinear with the centers of the round holes. In combination with these electrodes, a pair of masks for intercepting high-frequency energy from the normal cellular tissues contiguous to the affected part may also be used.

1 Claim, 21 Drawing Figures

Coolin pads not used
Electrodes energized for 4 minutes

Cooling pads used
Electrodes energized for 12 minutes

APPARATUS FOR HIGH-FREQUENCY HYPERTHERMIA

BACKGROUND OF THE INVENTION

The present invention is of use in the field of hyperthermia for tumors such as cancers, and especially for those which are located in the depth of the body of a patient. Thus, broadly, the invention relates to an improved apparatus for high-frequency hyperthermia to be used in the above-described field.

Hyperthermia, which consists of heating an affected part to a temperature ranging from 43° to 45° C. for a period of time ranging from a little over 10 minutes to several tens of minutes, has turned out to be effective in recent years as one of the therapies for a cancer or other tumor, namely, as one of the treatments for a part affected by abnormal cellular tissues. The effectiveness of hyperthermia has been clinically recognized.

High-frequency heating, which takes advantage of dielectric loss in a high-frequency field, is being regarded as a promising way of applying hyperthermia to an affected part located in the depth of the body of a patient.

FIG. 1 shows a conventional method of heating an affected part 2 which is located in the depth of the body 1 of a patient. A pair of electrodes 3 and 4 are attached to the surface of the body 1 so as to interpose the affected part 2 therebetween. Then the electrodes 3 and 4 are connected to a high-frequency generator 5, and high-frequency energy is supplied across the electrodes 3 and 4 with matched impedance obtained by a matching transformer 6. Thus the portion of the body 1 interposed between the electrodes 3 and 4 undergoes dielectric heating. During this dielectric heating, normal cellular tissues contiguous to the abnormal cellular tissues are kept under control so as to be kept at a temperature ranging from 40° to 42° C. Then the temperature of the affected part 2 becomes higher by 2° to 3° C. than the temperature of the normal cellular tissues, because the affected part 2 is poorly vascularized and the vascular system in this part is in a condition of circulatory insufficiency. This means that only the abnormal cellular tissues constituting the affected part 2 are heated to a higher temperature ranging from 43° to 45° C. and thereby necrosis occurs in these tissues. It stands to reason, therefore, that one entertains great expectations of the therapeutic effect of hyperthermia on such an affected part as mentioned above.

The trouble is that there is a danger of inflicting a burn upon the surface of the body 1 to which the electrodes 3 and 4 are attached. In order to eliminate this danger, it is most common, as shown in FIG. 2, to interpose a pad between each electrode and the surface of the body 1. Cold water is put in circulation through the pads 7 and 8 so that the surface of the body 1 may be cooled thereby during the above-described high-frequency heating.

The electrodes 3 and 4 used in any of the above-described conventional apparatuses are of a disc type as shown in FIG. 3 and constitute a pair of parallel planar electrodes, each of which has an exactly or nearly round rim. High-frequency energy supplied across the electrodes of this type is inevitably dispersed as shown with a plurality of broken lines A in FIG. 4 which illustrate the distribution of lines of force. The dispersion extends over such a wide range that the high-frequency energy cannot be concentrated on the affected part 2.

Thus the conventional apparatuses have a disadvantage that it is very difficult to heat only the affected part 2 to a sufficient degree, and a wide range of the normal cellular tissues contiguous to the affected part 2 is concurrently heated, not to say burnt.

SUMMARY OF THE INVENTION

It is an object of the present invention to provide an apparatus for high-frequency hyperthermia, which is capable of concentrating high-frequency energy on an affected part located in the depth of the body of a patient.

It is another object of the present invention to provide an apparatus for high-frequency hyperthermia, which is capable of preventing the normal cellular tissues contiguous to the affected part from being exposed to the high-frequency energy.

The first object of the present invention is accomplished by providing electrodes of an improved type, while the second object of the present invention is accomplished by providing masks, which are used in combination with the improved electrodes so as to intercept high-frequency energy from the normal cellular tissues contiguous to the affected part.

Other and further details of the present invention are hereinafter described with reference to the accompanying drawings.

DESCRIPTION OF THE PREFERRED EMBODIMENTS

Figure 5:
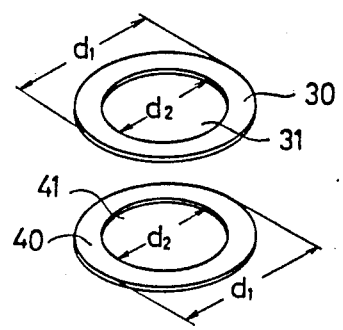
FIGS. 5 and 6 are perspective views of two pairs of annular electrodes used in the first embodiment of this invention.
Figure 7:
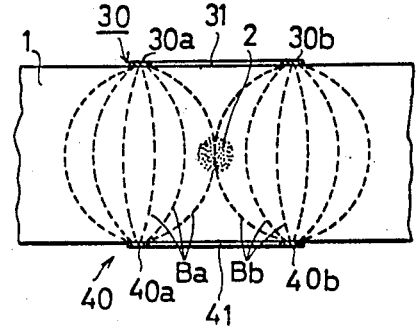
FIGS. 7 and 8 are vertical sections, illustrating how the lines of force are distributed therein.
Figure 6:
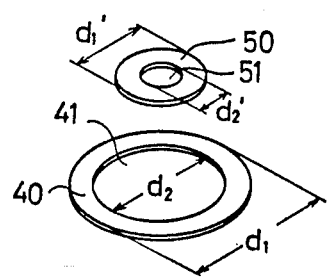
Figure 8:
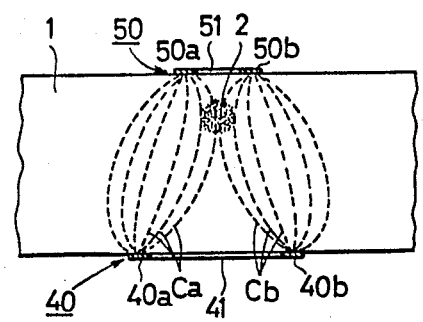

Referring now to the first embodiment of this invention, a pair of electrodes 30 and 40 shown in FIG. 5 and another pair of electrodes 40 and 50 shown in FIG. 6 have round holes 31, 41 and 51, respectively, so that the electrodes 30, 40 and 50 may be annularly shaped. These electrodes are made of thin plates because the thickness of an electrode has nothing to do with the heating efficiency. The electrodes 30 and 40 are equal in size, having an outside diameter of $d_1$ and an inside diameter of $d_2$. The electrode 50 having an outside diameter of $d_1'$ and an inside diameter of $d_2'$ is smaller than the electrodes 30 and 40. As shown in FIG. 7, the electrodes 30 and 40 are attached to the surface of the body 1 so as to be disposed opposite to each other in such a manner that the affected part 2 is allowed to lie on a straight line by which the centers of the holes 31 and 41 are linked with each other. As shown in FIG. 8, the electrodes 40 and 50 are attached to the surface of the body 1 so as to be disposed opposite to each other in such a manner that the affected part 2 is allowed to lie on a straight line by which the centers of the holes 41 and 51 are linked with each other. For a reason mentioned in the latter part of this specification, the above-described first embodiment of this invention presupposes that a pair of cooling pads should be used at the time of application.

Let it be imagined that the electrodes 30 and 40 are respectively made up of numerous fragments of an electrode material. Two of the imaginary fragments constituting the electrode 30 are designated as 30a and 30b in FIG. 7. These two imaginary fragments are kept away from each other by a distance equal to the inside diameter $d_2$ of the hole 31. On the other hand, two of the imaginary fragments constituting the electrode 40 are designated as 40a and 40b in FIG. 7. These two imaginary fragments are kept away from each other by a distance equal to the inside diameter $d_2$ of the hole 41 and are disposed in such a manner that, together with the imaginary fragments 30a and 30b, they constitute two pairs of parallel planar electrodes, wherein each pair of electrodes face to each other with the body 1 therebetween and one pair of electrodes are kept away from the other pair by the distance $d_2$. Let it be supposed that high-frequency energy is separately supplied across the electrodes 30a and 40a and across the electrodes 30b and 40b. Then the lines of force exerted between the electrodes 30a and 40a are distributed as shown with a plurality of broken lines Ba, while the lines of force exerted between the electrodes 30b and 40b are distributed as shown with a plurality of broken lines Bb. The range within which the lines of force Ba are distributed is in contact with the range within which the lines of force Bb are distributed. Since these two ranges are designed to be in contact with each other in such a manner that the point of contact falls in the affected part 2, the affected part 2 comes under the influence of both the high-frequency field produced by the electrodes 30a, 40a and that produced by the electrodes 30b, 40b. Thus the affected part 2 can get a supply of high-frequency energy from both fields.

Since the electrodes 30a, 30b and the electrodes 40a, 40b are the imaginary fragments of the annular electrodes 30 and 40, respectively, the electrodes 30 and 40 can be considered to be the aggregates of a large number of such imaginary fragments arranged annularly so as to be adapted to produce an annular arrangement of a large number of high-frequency fields of the above-described type. The affected part 2 is surrounded by such an annular continuum of high-frequency fields so as to come under the influence of a large number of high-frequency fields and thereby get a supply of high-frequency energy from the inside perimeters of all of these fields.

Figure 3:
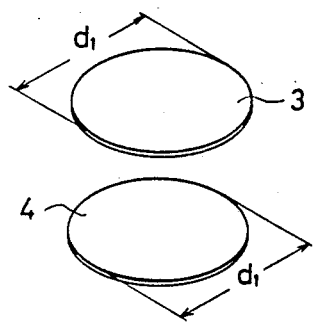
FIG. 3 is a perspective view of a pair of disc type electrodes used therein.
Figure 4:
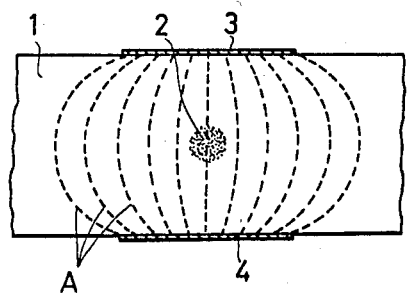
FIG. 4 is a vertical section, illustrating how the lines of force are distributed therein.

Although the high-frequency energy supplied across the annular electrodes 30 and 40 is dispersed around the affected part 2 as widely as is the case with conventional apparatuses, a portion, if not all, of this energy is concentrated on the affected part 2 as if it were brought into focus on the affected part 2, so that much more energy can be supplied thereto than to the remaining part of the body 1. Therefore, as compared with conventional apparatuses using disc type electrodes shown in FIG. 3, the first embodiment of this invention is capable of efficiently and sufficiently heating the affected part 2 which is located in the depth of the body 1.

In case of the construction shown in FIG. 7, electrodes 30 and 40 equal in size are used. With these electrodes, high-frequency energy can be concentrated only on an area which is located in the middle of the thickness of the body 1, and an affected part 2 can be effectively heated only when it is located in this area.

In case of the construction shown in FIG. 8, electrodes 40 and 50 different in size as shown in FIG. 6 are used. On the basis of the same supposition as is the case with FIG. 7, two of the imaginary fragments constituting the electrode 50 are designated as 50a and 50b. The lines of force exerted between the electrodes 40a and 50a are distributed as shown with a plurality of broken lines Ca, while the lines of force exerted between the electrodes 40b and 50b are distributed as shown with a plurality of broken lines Cb. The range within which the lines of force Ca are distributed is in contact with the range within which the lines of force Cb are distributed. As compared with the construction shown in FIG. 7, the area in which these two ranges are in contact with each other (i.e., the area on which high-frequency energy can be concentrated) is disposed nearer to the smaller electrode 50 (i.e., above the middle of the thickness of the body 1 in FIG. 8). Therefore, an affected part 2 can be effectively heated only when it is located in an area deviating from the middle of the thickness of the body 1. The area on which high-frequency energy can be concentrated is allowed to deviate therefrom to such an extent as to be determined by the difference between the size of the electrode 40 and that of the electrode 50.

By suitably selecting the size of one electrode relative to the size of the other, the area on which high-frequency energy is to be concentrated can be set at any depth of the body 1 in case of the construction shown in FIG. 8, so that an affected part 2 can be most properly heated according to its site.

Figure 1:
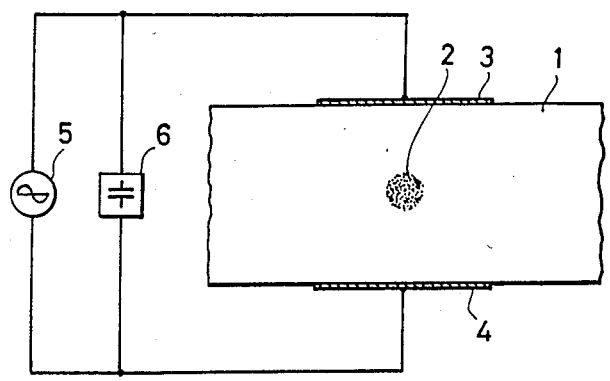
FIGS. 1 and 2 are vertical sections of conventional apparatuses.
Figure 2:
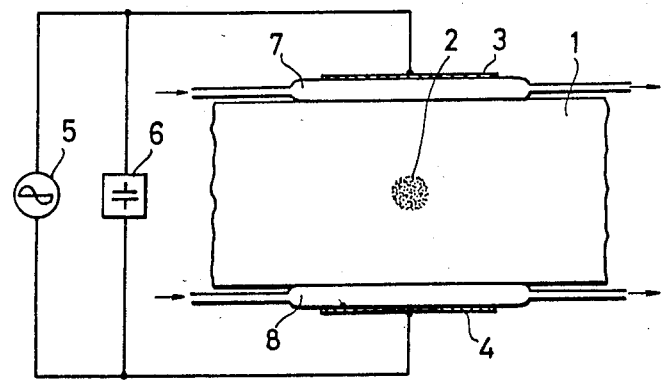
Figure 10:
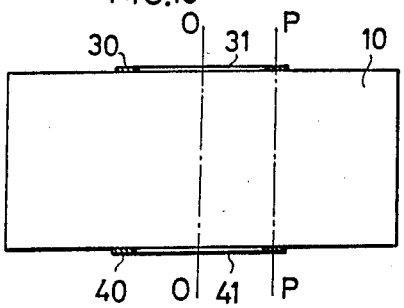
FIGS. 9 to 11 are vertical sections of arrangements made for conducting various comparative studies.
Figure 11:
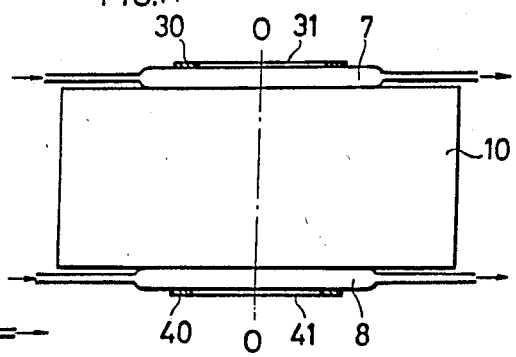
Figure 9:
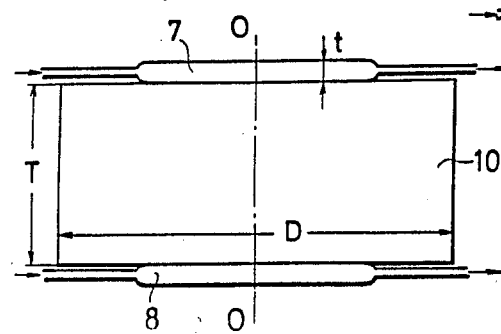

Referring now to FIGS. 9 to 11, the annular electrodes 30 and 40 equal in size as shown in FIG. 5 are attached to the surface of an inanimate model 10 of the living body 1. The aims of this construction are to study the difference between the heating effect of conventional disc type electrodes and that of the annular electrodes of this invention, to study how the heating effect is affected by the difference in the inside diameters of annular electrodes having an equal outside diameter, and to study the effects of the electrodes under the condition that the pads 7 and 8 shown in FIG. 2 are used in combination with the electrodes.

The following are used for the above-described studies: (1) The model 10 made of agar-agar in the shape of a low column having a height T of 17 cm and a diameter D of 36 cm. (2) A pair of annular electrodes 30 and 40 having an outside diameter $d_1$ of 16 cm and an inside diameter $d_2$ of 10 cm. (3) Another pair of annular electrodes 30 and 40 having an outside diameter $d_1$ of 16 cm and an inside diameter $d_2$ of 12 cm. (4) A pair of conventional disc type electrodes shown in FIG. 3, to be used as a control, having a diameter $d_1$ of 16 cm. (5) The pads 7 and 8 having a thickness t of 2 cm and a diameter larger than $d_1$ and adapted to allow cold water to circulate therethrough. The cold water, which is kept under temperature control so as to be kept at 6° C., and the model 10 contain 0.4% by weight NaCl so as to be made electrically equivalent to the muscles of the living body 1.

The model 10 was heated by high-frequency energy supplied at 13.56 MHz across a pair of electrodes. Thermographs well known in the art as conventional thermometric apparatuses were used for making investigation into the temperature pattern of the model 10. Graphs were prepared on the basis of numerical values obtained from the analysis of monitored pictures.

Figure 12:
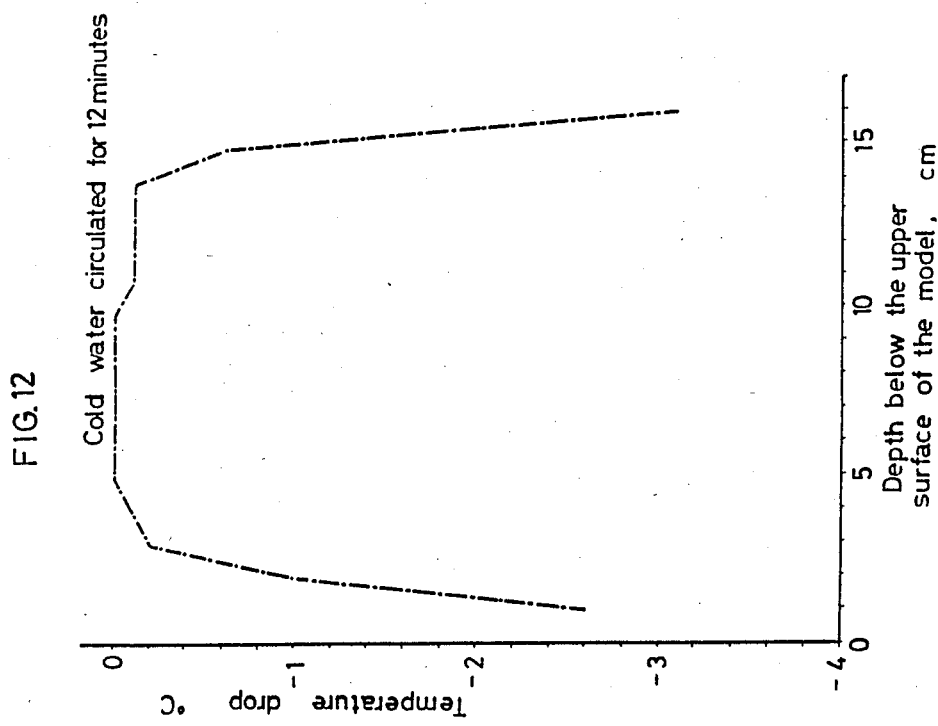
FIG. 12 is a graphical representation of the cooling effect of pads used therein.

In the first place, investigation into the cooling effect of the pads 7 and 8 was made by attaching the pads 7 and 8 to the upper and lower surfaces, respectively, of the model 10 as shown in FIG. 9, by allowing the cold water kept at 6° C. to circulate for 12 minutes through the pads 7 and 8, and by measuring the temperatures at various points within the model 10 in order to check the temperature drops after the lapse of the above-mentioned 12 minutes. The points at which the temperatures were measured were disposed along the axis O—O of the model 10, and the depths of these points below the upper surface of the model 10 were determined in such a manner that they increased in arithmetical progression. FIG. 12 shows a graphical representation of the results of this investigation.

The findings shown in FIG. 12 suggest that the pads 7 and 8 have a cooling effect only within the limits of about 3 cm in depth below the upper surface and above the lower surface of the model 10 and hardly have a cooling effect on the deeper portion.

Figure 13:
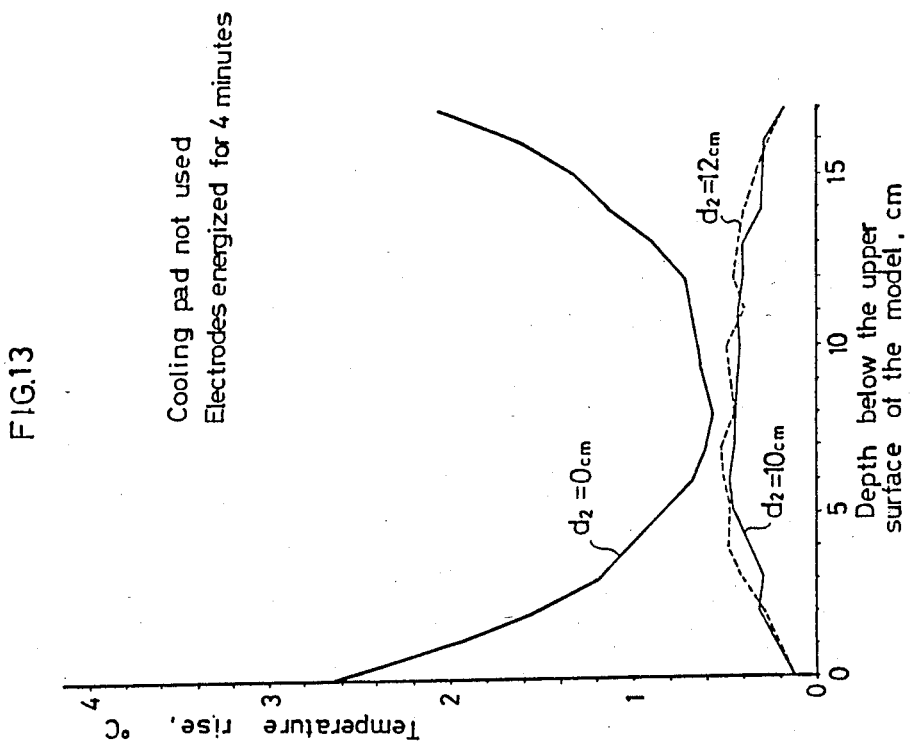
FIGS. 13 and 14 are graphical representations of the heating effects of the annular electrodes under the condition that the cooling pads are not used.

In the second place, investigation into the heating effects of dielectric heating in a high-frequency field was made by directly attaching the annular electrodes 30 and 40 to the upper and lower surfaces, respectively, of the model 10 without using the pads as shown in FIG. 10. A pair of annular electrodes having an inside diameter $d_2$ of 10 cm and another pair of annular electrodes having an inside diameter $d_2$ of 12 cm were respectively energized for 4 minutes under the above-described condition. Then the temperatures were measured at various points within the model 10 in order to check the temperature rises after the lapse of the above-mentioned 4 minutes. The points at which the temperatures were measured were disposed along the axis O—O of the model 10, and the depths of these points below the upper surface of the model 10 were determined in such a manner that they increased in arithmetical progression. FIG. 13 shows a graphical representation of the results of this investigation. For comparative purposes, the results of measurement conducted with conventional disc type electrodes are also shown in FIG. 13 in the form of a polygonal line designated as $d_2=0$ cm.

The findings shown in FIG. 13 suggest that the disc type electrodes have a heating effect only on the portions close to the upper and lower surfaces of the model 10 and tend to be remarkably deteriorated in the heating effect on the deeper portion, and that the heating effect of the annular electrodes shows itself contrariwise, i.e., it tends to become gradually greater in proportion to the distance measured in the inward direction from the upper and lower surfaces of the model 10.

Figure 14:
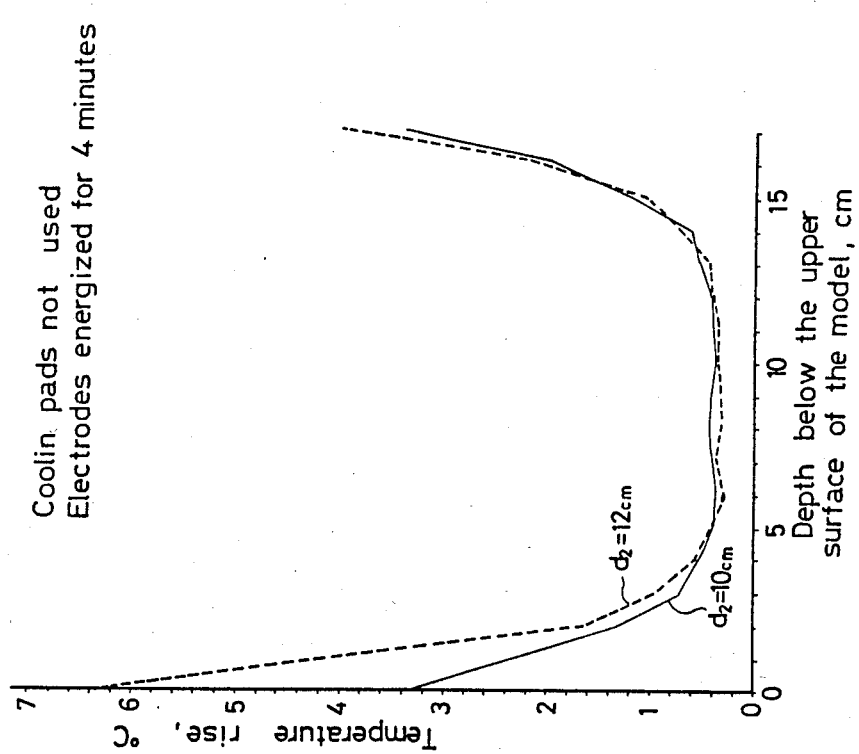

In the third place, investigation into the heating effects was made with the electrodes likewise energized for 4 minutes and with the temperatures thereafter measured at various points along line P—P of FIG. 10, which was defined as a line running parallel with the axis O—O substantially at a distance $(d_1+d_2)/2$ therefrom. FIG. 14 shows a graphical representation of the results obtained from a pair of annular electrodes 30 and 40 having an inside diameter $d_2$ of 10 cm and another pair of annular electrodes 30 and 40 having an inside diameter $d_2$ of 12 cm.

The findings shown in FIG. 14 suggest that, as far as the heating effect is measured along the above-defined line P—P, the findings obtained from the conventional disc type electrodes and shown in FIG. 13 with the polygonal line designated as $d_2=0$ cm hold true for the annular electrodes 30 and 40 as well. Namely, the annular electrodes 30 and 40 have a heating effect only on the portions close to the upper and lower surfaces of the model 10 and tend to be remarkably deteriorated in the heating effect on the deeper portion. An explanation for the analogy between the polygonal line $d_2=0$ cm in FIG. 13 and the polygonal lines in FIG. 14 is provided by the supposition mentioned earlier in connection with FIG. 7, in which the annular electrodes 30 and 40 were considered to be the aggregates of a large number of imaginary fragments arranged annularly so that each pair of such imaginary fragments lying on a vertical plane, such as 30a, 40a or 30b, 40b, may constitute a pair of parallel planar electrodes.

Figure 15:
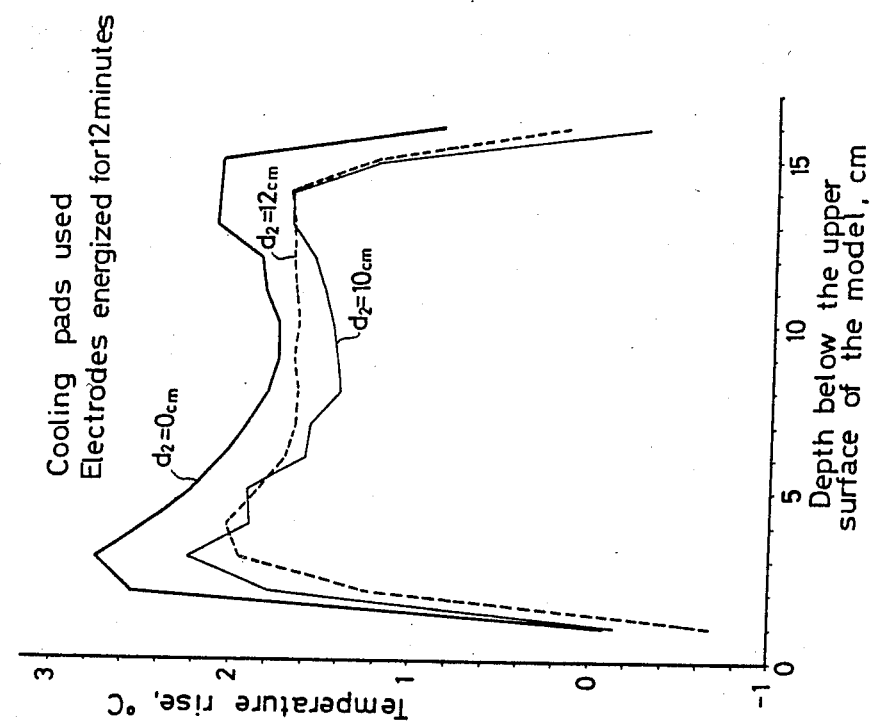
FIG. 15 is a graphical representation of the heating effects of the annular electrodes under the condition that the cooling pads are used.

In the fourth place, investigation into the heating effect was made by attaching the annular electrodes 30 and 40 to the upper and lower surfaces, respectively, of the model 10 with a pad interposed between each electrode and the surface of the model 10 as shown in FIG. 11, by energizing the electrodes for 12 minutes, and by measuring the temperatures at various points within the model 10 in order to check the temperature rises after the lapse of the above-mentioned 12 minutes. The points at which the temperatures were measured were disposed along the axis O—O of the model 10, and the depths of these points below the upper surface of the model 10 were determined in such a manner that they increased in arithmetical progression. FIG. 15 shows a graphical representation of the results of this investigation. In FIG. 15, the results of measurement conducted with a pair of annular electrodes having an inside diameter $d_2$ of 10 cm, another pair of annular electrodes having an inside diameter $d_2$ of 12 cm, and a pair of conventional disc type electrodes ($d_2=0$ cm) are individually shown for comparative purposes.

The findings shown in FIG. 15 suggest that, because the electrodes were energized for as long as 12 minutes, their heating effects are generally greater in FIG. 15 than in FIG. 13. However, in the range of 2 cm in depth below the upper surface and above the lower surface of the model 10, the heating effects are restrained by the pads to such an extent that the temperature of the model 10 rises only slightly or even drops at some points. This is caused by the cooling effect of the pads on the above-described range of the model 10. Namely, the heating effects of the electrodes are partially offset by the cooling effect of the pads in this range. In addition, the electrodes are kept away from the surfaces of the model 10 by a distance equivalent to the thickness t of each pad. Consequently, the vicinity of each electrode where the density of the lines of force is especially high is correspondingly kept away from the model 10. This is another cause of the restrained heating effects of the electrodes on the above-described range of the model 10.

The findings shown in FIG. 15 further suggest that the annular electrodes show much the same trend as the disc type electrodes in the manifestation of heating effects. Namely, the range of 3 to 5 cm in depth below the upper surface and above the lower surface of the model 10 tends to be more easily heated than the deeper range by the electrodes of both types. This is probably because the heating effects centering around the above-defined line P—P (FIG. 10) extend to the vicinity of the axis O—O. However, the annular electrodes are not so extreme as the disc type electrodes in the manifestation of the above-described trend. Only a slight temperature difference is caused by the annular electrodes between the above-described two ranges, i.e., between the range of 3 to 5 cm in depth below the upper surface and above the lower surface of the model 10 on one hand and the deeper range on the other hand.

In order to present data in a more conspicuous form, reference will now be made to FIGS. 16 and 17, in which the heating effect measured at each point along the axis O—O of the model 10 is expressed in terms of the ratio of the temperatures rise measured at that point to the highest temperature rise found along the axis O—O.

Figure 16:
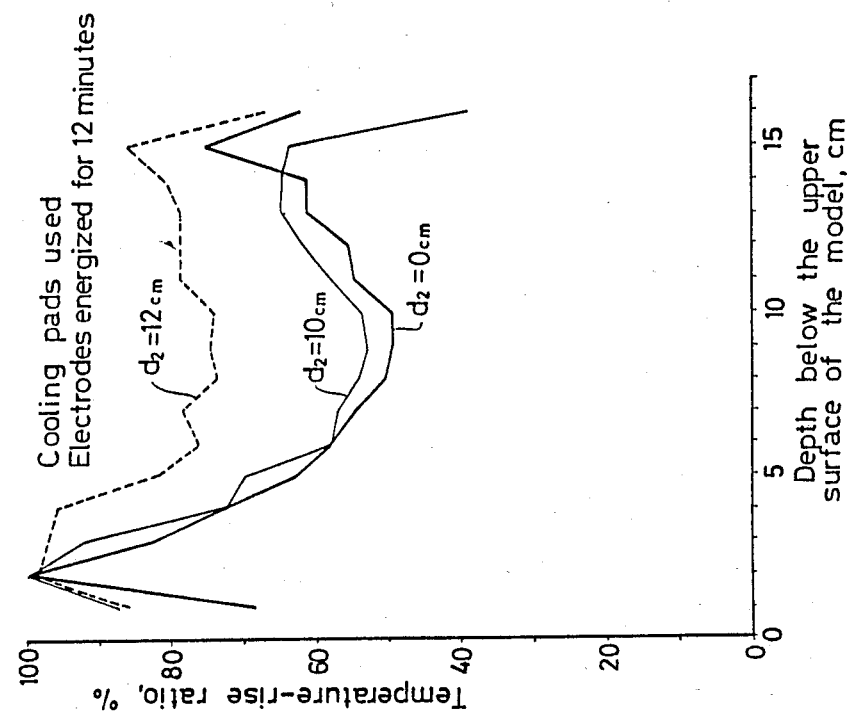
FIGS. 16 and 17 are graphical representations, wherein the heating effect measured at each measuring point along the axis of an inanimate model of the living body and shown in FIGS. 13 and 15, respectively, is expressed in terms of the ratio of the temperature rise measured at that measuring point to the highest temperature rise found along the axis of the model.
Figure 17:
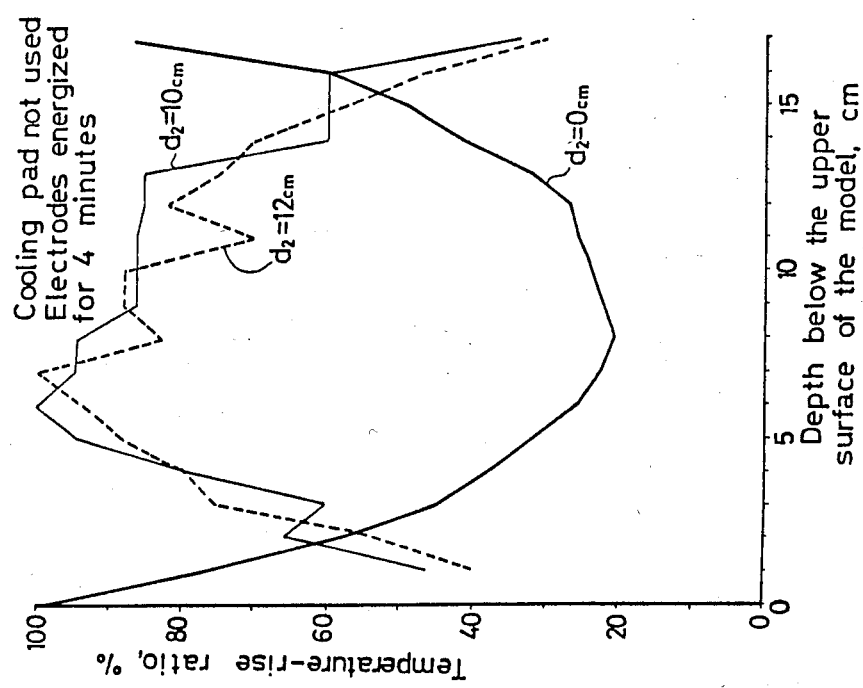

FIGS. 16 and 17 were obtained when the results of the investigations shown in FIGS. 13 and 15, respectively, were converted in the manner mentioned in the preceding paragraph. The highest temperature rise found along the axis O—O of the model 10 is indicated by an index number of 100%. In order to determine the extent to which the heating effects are affected by the electrodes kept away from the surfaces of the model 10 by a distance equivalent to the thickness of each pad, data in FIG. 15 were corrected by taking account of the data in FIG. 12 so that the influence exerted by the cooling effect of the pads on the heating effects of the electrodes might by excluded from FIG. 17.

FIGS. 16 and 17 reveal that, although the ratio of the temperature rise in the middle of the thickness along the axis O—O of the model 10 is as low as about 20% when the disc type electrodes ($d_2=0$ cm) are kept in touch with the surfaces of the model 10, the ratio comes up to about 50% when the disc type electrodes are kept away from the surfaces of the model 10 by a distance equivalent to the thickness of each pad. FIGS. 16 and 17 further reveal that, in contrast with such an increase in the ratio found in case of the disc type electrodes kept away from the surfaces of the model 10 as compared with those kept in touch with the surfaces of the model 10, the ratio of the temperature rise in the middle of the thickness along the axis O—O of the model 10 is decreased in case of the annular electrodes kept away from the surfaces of the model 10 as compared with those kept in touch with the surfaces of the model 10. However, when the annular electrodes are kept away from the surfaces of the model 10, the portions of the model 10 close to its upper and lower surfaces along the above-defined line P—P are prevented from being excessively heated. From this finding, it may be concluded that the employment of pads is one of the necessary conditions for the first embodiment of this invention.

FIGS. 16 and 17 still further reveal that, even under the influence of the cooling effect of the pads, the ratio of the temperature rise in the middle of the thickness along the axis O—O of the model 10 is higher in case of the annular electrodes than in case of the disc type electrodes. It will be worthy of special mention that the ratio can be maintained at 75% when the annular electrodes having an inside diameter $d_2$ of 12 cm are used.

From the foregoing it will be readily understood that, for the purpose of taking advantage of dielectric loss in a high-frequency field when heating an affected part which is located in the depth of the body of a patient, the annular electrodes are more effective than the disc type electrodes, and especially the annular electrodes having a larger inside diameter $d_2$ are more effective than those having a smaller inside diameter $d_2$ while having an equal outside diameter $d_1$.

The problem with the above-described first embodiment of the present invention is that the annular electrodes 30 and 40 unnecessarily heat the model 10 along the above-defined line P—P. This problem is solved by the second embodiment of the present invention, which provides masks adapted to intercept high-frequency energy from the normal cellular tissues contiguous to the affected part.

Although two annular electrodes used in the first embodiment of the present invention constitute a pair of parallel planar electrodes, they can also be regarded as antennas individually irradiating electromagnetic waves. Based on this viewpoint, the second embodiment of the present invention provides masks adpated to restrict the range of exposure to the electromagnetic waves irradiated by the antennas and thereby inhibit the dispersion of the electromagnetic waves to the area which need not or should not be exposed thereto. Thus the second embodiment of the present invention is capable of concentrating the electro-magnetic waves, in so far as possible, on an affected part which is located in the depth of the body of a patient.

Figure 18:
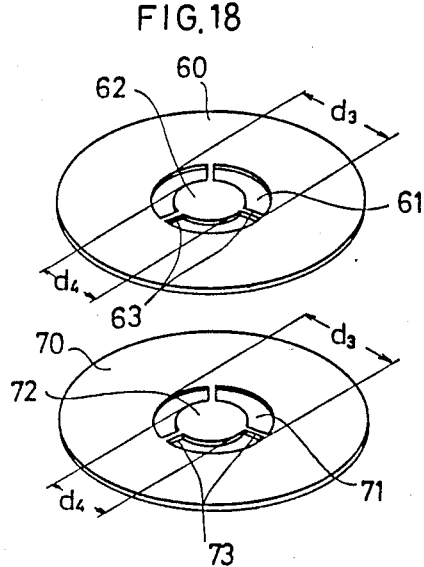
FIG. 18 is a perspective view of a pair of masks used in the second embodiment of this invention for intercepting high-frequency energy from normal cellular tissues contiguous to an affected part.
Figure 19:
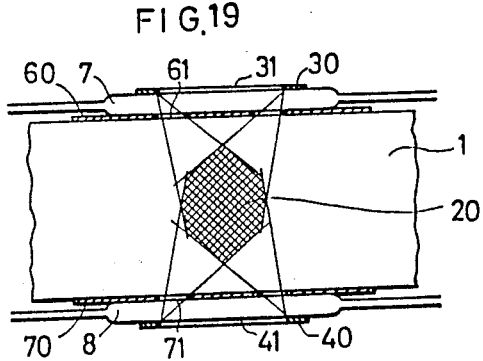
FIGS. 19 to 21 are vertical sections, illustrating the ranges on which the irradiated electromagnetic waves are concentrated by the masks.
Figure 20:
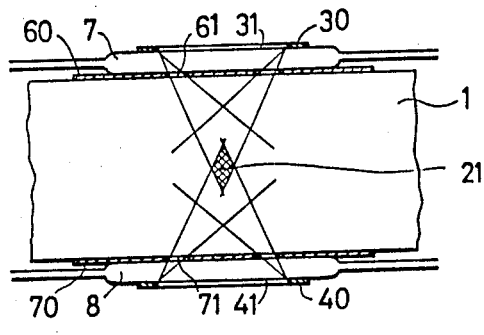
Figure 21:
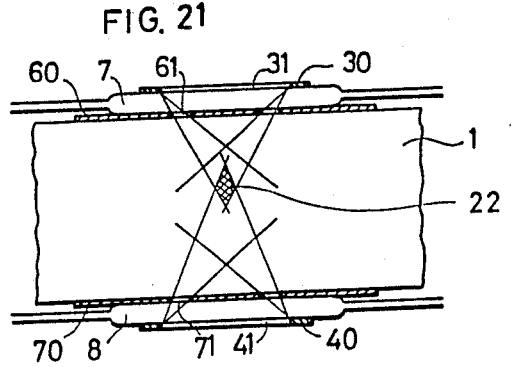

The masks 60 and 70 used in the second embodiment of the present invention are made of a tabular material having an excellent property of intercepting high-frequency energy. Polytetrafluoroethylene (commonly known by the trade name "Teflon") is one of the materials having such a property. As shown in FIG. 18, annular slits 61 and 71 are formed in the masks 60 and 70, respectively, in such a manner that core parts 62 and 72 remain connected to the main parts of the masks 60 and 70, respectively, by a plurality of slender bridge members 63 and 73 or the like, which are disposed radially by way of example so as to divide the annular slits 61 and 71 into a plurality of arc-shaped slits. Nevertheless, the slits 61 and 71 can be regarded as annular continua in the sense that the bridge members 63 and 73 or the like are so slender that they are not obstructive to the irradiation of electromagnetic waves. As shown in FIGS. 19 to 21, each mask is interposed between each cooling pad and the surface of the body 1 in such a manner that the annular slits 61 and 71 are trued up coaxially with the round holes 31 and 41, respectively, of the annular electrodes 30 and 40. The masks 60 and 70 have a much larger diameter than the annular electrodes 30 and 40 to the extent of being equal in size to, or even larger than, the cooling pads 7 and 8. On the other hand, the outside diameter $d_3$ of the annular slits 61 and 71 is smaller than the inside diameter $d_2$ of the annular electrodes 30 and 40 and, as a matter of course, the inside diameter $d_4$ of the annular slits 61 and 71 is still smaller.

Referring now to FIG. 19, electromagnetic waves irradiated by the annular electrodes 30 and 40 perpendicularly to the surface of the body 1 are intercepted by the main parts of the masks 60 and 70, respectively, and prevented from infiltrating into the body 1.

Because of the cooling pad 7 interposed between the electrode 30 and the mask 60, and because of the cooling pad 8 interposed between the electrode 40 and the mask 70, the electrodes 30 and 40 are kept away from the surfaces of the masks 60 and 70, respectively, by a distance equivalent to the thickness t of each pad. Consequently, electromagnetic waves irradiated by the electrodes 30 and 40 penetrate through the pads 7 and 8, respectively, and only obliquely infiltrate into the body 1 after passage through the annular slits 61 and 71 of the masks 60 and 70, respectively. Because the outside diameter $d_3$ of the slits 61 and 71 is smaller than the inside diameter $d_2$ of the electrodes 30 and 40, and because the slits 61 and 71 are trued up coaxially with the round holes 31 and 41, respectively, of the electrodes 30 and 40, electromagnetic waves irradiated by the electrodes 30 and 40 and obliquely infiltrating into the body 1 through the slits 61 and 71, respectively, are concentrated on a portion 20 denoted by a net pattern in FIG. 19. Thus the electromagnetic waves are inhibited from dispersion to the area other than the portion 20.

The smaller the ratio of $d_3$ to $d_2$ is, the smaller the portion 20 becomes in size. If one takes advantage of this rationale, a reduced portion 21 on which the electromagnetic waves are concentrated in the body 1 is obtained as shown with a net pattern in FIG. 20.

In case of the construction shown in FIGS. 19 and 20, the slits 61 and 71 are equal in the outside diameter $d_3$. Consequently the portions 20 and 21, on which the electromagnetic waves are concentrated, are located in the middle of the thickness of the body 1, and only an affected part located in this area can be effectively heated by the high-frequency energy concentrated thereon.

If the slits 61 and 71 are different in the outside diameter $d_3$, the area on which the electromagnetic waves are concentrated is allowed to deviate from the middle of the thickness of the body 1. For example, if the slit 61 has a smaller outside diameter $d_3$ than the slit 71, a portion 22 on which the electromagnetic waves are concentrated is disposed nearer to the slit 61 as shown in FIG. 21. Thus the portion 22 can be positioned at one's desire by suitably selecting the outside diameter $d_3$ of the slit 61 relative to that of the slit 71, so that even an affected part located in an area deviating from the middle of the thickness of the body 1 can be effectively heated by the high-frequency energy concentrated thereon.

The portion 22 is allowed to deviate all the more if the electrodes 40 and 50 different in size as shown in FIG. 6 are used, if the mask 60 is disposed on the same side as the smaller electrode 50, and if the slit 61 has a still smaller outside diameter than the inside diameter $d_2'$ of the smaller electrode 50.

In case of the construction shown in FIGS. 20 and 21, the inside diameter $d_4$ of the annular slits 61 and 71 does not contribute to the concentration of electromagnetic waves on an affected part, although the diameter $d_4$ makes some contribution to inhibiting the dispersion of the electromagnetic waves to the area other than the affected part. In addition, when the smaller electrode 50 is used as mentioned in the preceding paragraph, there may be times when the inside diameter $d_4$ of the annular slit 61 has to be made extremely small in accordance with the inside diameter $d_2'$ of the smaller electrode 50. There might as well be times, therefore, when the inside diameter $d_4$ of the annular slit 61 is reduced to zero, i.e., the core part 62 is allowed to be missing.

From the foregoing, it will be apparent that in addition to the benefit or advantage provided by the first embodiment of this invention, the second embodiment of this invention further provides an efficient and useful means for inhibiting the dispersion of the high-frequency energy to the area other than an affected part so that the normal cellular tissues disposed along the above-defined line P—P may be protected from being unnecessarily heated.

When an investigation into the heating effect of the second embodiment was made in the same manner as mentioned in connection with FIG. 11, the results showed overt improvement in the undesirable tendency observed in FIG. 15, i.e., the tendency that the range of 3 to 5 cm in depth below the upper surface and above the lower surface of the model 10 tends to be more easily heated than the deeper range. Consequently, the ratio of the temperature rise in the middle of the thickness along the axis O—O of the model 10 to the highest temperature rise found along said axis (see FIG. 17) was also improved.

What is claimed is:

1. In an apparatus for high-frequency hyperthermia comprising a pair of electrodes connected to a high-frequency generator to produce a high-frequency field between said electrodes, and a pair of cooling pads each having opposed surfaces, there being one cooling pad associated with each of said electrodes, said electrodes being positionable on opposite sides of a body having an affected part therein so that the centers of the electrodes and said affected part may be aligned, and said cooling pads being positionable with one surface facing said electrodes and an opposed surface facing said body, the improvement wherein said electrodes are annularly shaped with a round hole therein, said improvement further comprising, a pair of masks made of a tabular material having a property of intercepting high-frequency energy, said masks having annular slits, the outside diameter of said annular slits being smaller than the inside diameter of said annular electrodes, each of said masks being positionable in coaxial alignment with the holes in said electrodes and adjacent the surface of a cooling pad which is opposed to the cooling pad surface facing its associated electrode.

* * * * *